(12) United States Patent
Marchesi

(10) Patent No.: US 6,366,816 B1
(45) Date of Patent: Apr. 2, 2002

(54) ELECTRONIC STIMULATION EQUIPMENT WITH WIRELESS SATELLITE UNITS

(76) Inventor: Fabio Paolo Marchesi, Via Tadino, 13, 20124 Milan (IT)

(*) Notice: Subject to any disclaimer, the term of this patent is extended or adjusted under 35 U.S.C. 154(b) by 0 days.

(21) Appl. No.: 09/468,299

(22) Filed: Dec. 21, 1999

(30) Foreign Application Priority Data

Dec. 23, 1998 (IT) ............................ MI98A2795

(51) Int. Cl.$^7$ ................................. A61N 1/36
(52) U.S. Cl. ..................................... 607/59
(58) Field of Search ................. 607/41, 39, 61

(56) References Cited

U.S. PATENT DOCUMENTS

| | | |
|---|---|---|
| 4,016,871 A | 4/1977 | Schiff |
| 5,540,235 A | 7/1996 | Wilson |
| 5,562,706 A | 10/1996 | Lauterbach et al. |
| 5,824,022 A | 10/1998 | Zilberman et al. |

*Primary Examiner*—William E. Kamm
(74) *Attorney, Agent, or Firm*—Shlesinger Fitzsimmons Shlesinger

(57) ABSTRACT

Electronic equipment for the production of stimuli for treatment of the human body comprises a base unit (11) and at least one satellite unit (13). The satellite unit comprises in turn a power supply battery (23) and means (21, 22) powered by this battery for producing an electric signal and applying it to a stimulus emission member (17) in response to said signal. The base unit (11) comprises means (28) for generating at least one actuation and de-actuation command for production of the electrical signal of the satellite unit (13) with the base unit and satellite units being connected by a wireless transmission for transfer of said command from one to the other.

12 Claims, 2 Drawing Sheets excellent # ELECTRONIC STIMULATION EQUIPMENT WITH WIRELESS SATELLITE UNITS

BACKGROUND OF THE INVENTION

The present invention relates to innovative electronic stimulation equipment for treatment of the human body. By 'stimulation equipment' is meant here equipment for application to the human body of stimuli produced by both direct and indirect electrical currents. The stimulus can be electrical, magnetic, luminous, heat, et cetera. Not only EMS (Electrical Muscle Stimulation) electrostimulators or TENS (Transcutaneous Nerve Stimulation) in which the electrical current is applied directly to the body are included but also equipment whose stimulation action is obtained through electrical or electromagnetic fields or through the emission of luminous radiation with predetermined frequencies for example in the infrared range.

Known equipment includes a control unit to which stimuli emission members such as electrodes of the type suited for the particular desired stimuli are connected by means of electrical wires. Since the number of members or electrodes can be relatively high the difficulties which can be encountered during their application to the body are evident. For example with direct electrostimulation produced by means of the difference in potential applied to a pair of electrodes there can be up to sixteen electrode pairs and therefore thirty-two electrical conductors usually at least a couple of meters long which connect the control unit to the user's body.

In addition to the possibility for the wires to tangle and knot together creating considerable confusion there is the objective impossibility for the user to move with a certain freedom. In addition it becomes difficult to recognize which electrodes are associated in a pair and which of the controls at the control unit correspond to a given pair.

This becomes particularly important when an operator or user wishes to individually regulate operating parameters of individual electrode pairs through the controls arranged on the control unit.

To reduce the difficulty of identification simple solutions have been offered in the prior art such as the use of wires of different colors for each emission member or electrode or electrode pair. In the case of direct electrical stimulation it has even been proposed to begin the treatment with all intensities at zero to then increase intensity one electrode pair at a time so that the contracting muscle on which electrode pair regulation is being done would be apparent.

Even when the intensities have been perfectly regulated at the beginning of a treatment, during an electrostimulation cycle further regulations can become necessary even due to the only fact that skin conductivity can vary for example because of perspiration produced by the physical activity resulting from the electrostimulation or even by the mere presence of the electrode which impedes perspiration.

The difficulty of these further regulations is evident especially in the frequent case when the user is left alone and therefore must make the regulation himself with the obstacle of the connecting wires and the difficulty of associating an electrode pair with the corresponding regulation control. In some professional versions of electrostimulation equipment a remote control is provided through which the subject himself undergoing the session can independently regulate the intensity of the electrical impulses without having to reach the equipment control console. But the difficulty of finding the association between electrode pairs whose effect it is desired to regulate and regulation control remains.

The general purpose of the present invention is to overcome the above shortcomings by supplying electronic stimulation equipment in which the need for cumbersome connecting wires is eliminated.

SUMMARY OF THE INVENTION

In view of this purpose it is sought to provide in accordance with the present invention electronic equipment for the production of stimuli for treatment of the human body comprising a base unit and at least one satellite unit with the satellite unit comprising in turn a power supply battery and means powered by this battery for producing an electric signal and applying it to a stimuli emission member in response to said signal with the base unit comprising means of generating at least one actuation and de-actuation command for production of the electrical signal of the satellite unit with the base unit and satellite units being connected by a wireless transmission for the transfer of said command from one to the other.

BRIEF DESCRIPTION OF THE DRAWINGS

To clarify the explanation of the innovative principles of the present invention and its advantages compared with the prior art there is described below with the aid of the annexed drawings a possible embodiment thereof by way of non-limiting example applying said principles. In the drawings.

DETAILED DESCRIPTION OF THE INVENTION

Figure 1:
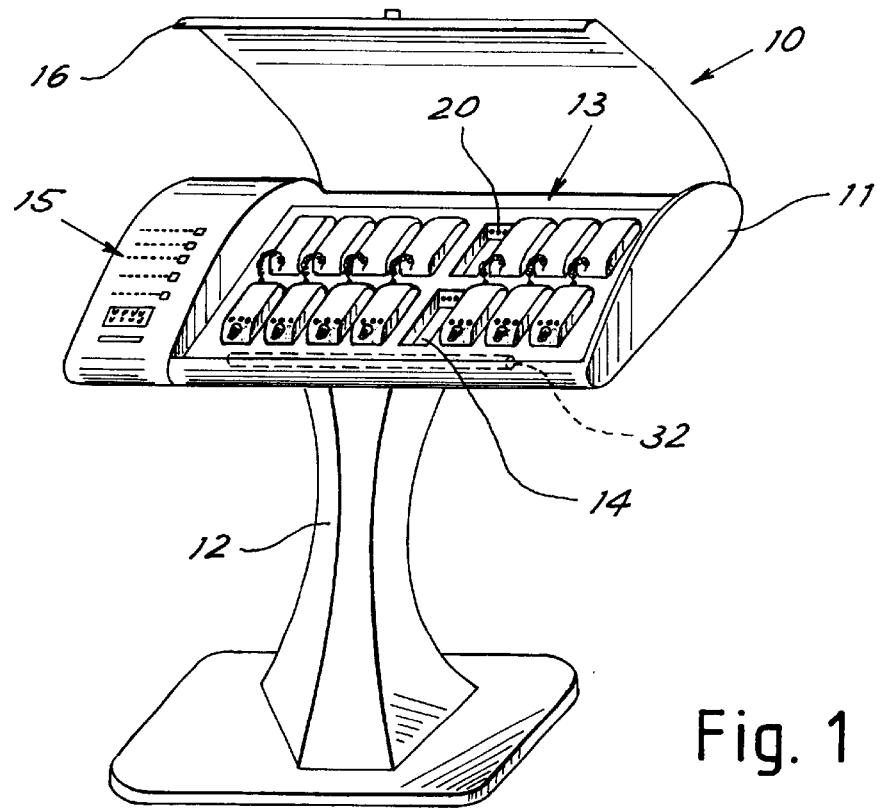
FIG. 1 shows a diagrammatic perspective view of stimulation equipment in accordance with the present invention.

With reference to the figures, FIG. 1 shows electronic stimulation equipment indicated as a whole by reference number 10 comprising a base unit 11 for example equipped with a pedestal 12 and a plurality of satellite units 13 which are received in purposeful seats 14 in the base unit when not in use. The base unit comprises a control panel 15 and if necessary a closing cover 16 for the zone receiving the satellite units.

Figure 2:
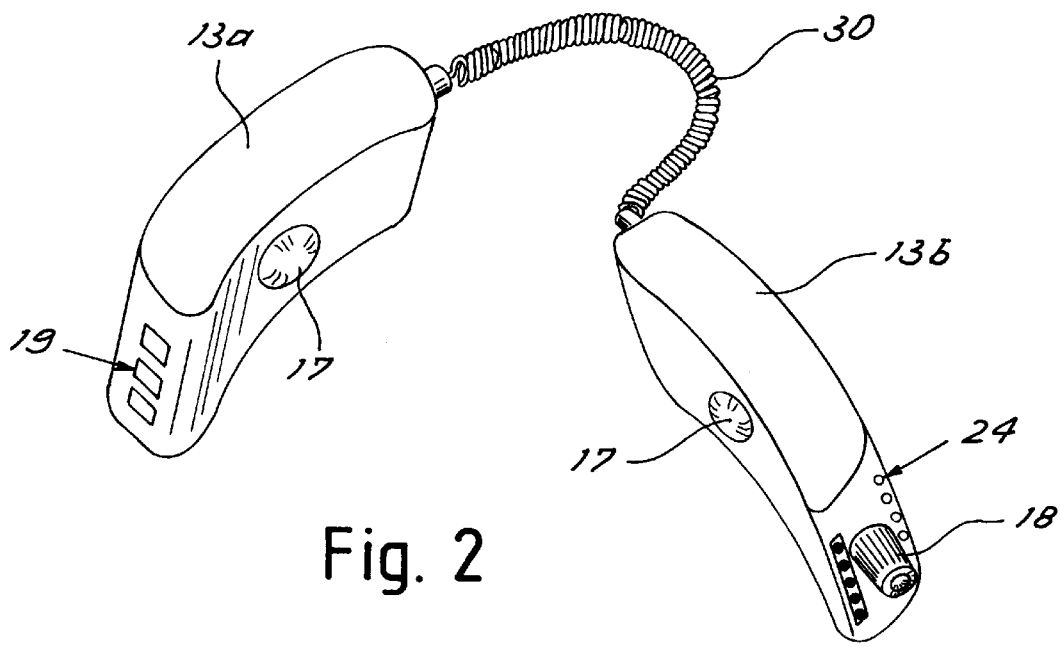
FIG. 2 shows a diagrammatic perspective view of a satellite unit of the equipment of FIG. 1.

As shown in FIG. 2 each satellite unit 13 comprises members 17 readily imaginable by one skilled in the art for electrical, magnetic, luminous, calorific et cetera stimuli emissions to be applied to the body undergoing treatment. For the sake of simplicity the emission members will be indicated as electrodes 17 in particular for the emission of type EMS or TENS electrical stimuli. Unit 13 comprises stimuli intensity regulation controls 18.

For direct electrostimuli by means of electrical current the electrodes are made up of a pair of conductive members which embody a reference electrode and an active electrode. Advantageously to allow adequate positioning of the electrodes of a pair the satellite unit 13 is made up of two parts or sub-units 13a and 13b interconnected by a short electrical wire 30 advantageously coiled. Each part of the satellite unit supports one electrode of the pair. In this manner it is possible to position the two electrodes of the pair in the most appropriate position on the body. Elastic bands not shown permit keeping the satellite unit in the selected position on the body.

Each satellite unit 13 has electrical contacts 19 which are paired with complementary electrical contacts 20 located in the housing seats in the base unit when the satellite unit is placed in the seat.

Figure 3:
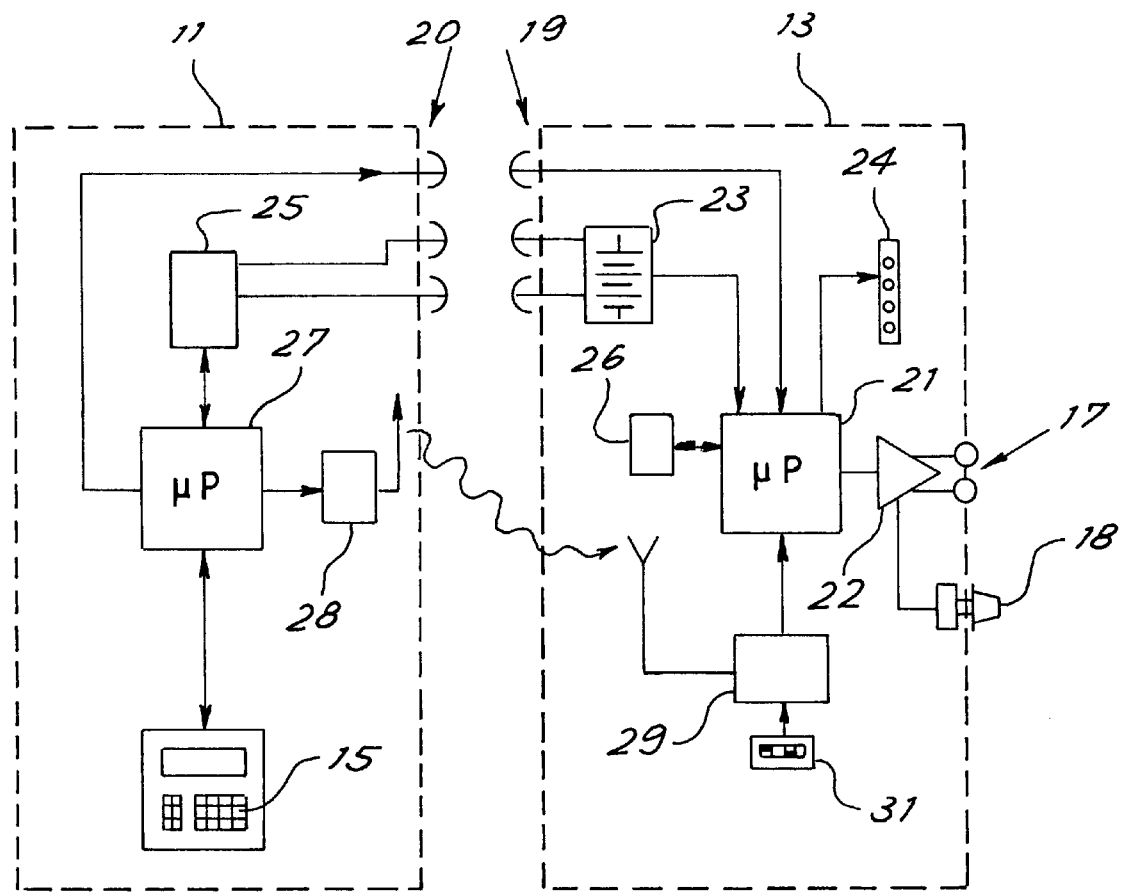
FIG. 3 shows a block diagram of a base unit and a satellite unit of the equipment of FIG. 1.

As may be seen in FIG. 3 each satellite unit includes within it an electrical battery 23 for independent powering and an electronic circuit for production of the electrical signals to be applied to the members 17.

In particular the electronic circuit can advantageously be provided with an appropriately programmed microprocessor 21 for generating control signals for a power amplifier 22 with outlet connected to the electrodes. The regulation controls 18 can control the amplitude of the signals applied to the electrodes.

The circuit 21 can also control a display 24 for example comprising light emitting diodes.

The electrical contacts 19 can be employed for supplying recharging power for the batteries 23 provided in the form of accumulators when the satellite unit is in the seat 14. For this purpose the base unit 11 comprises a battery charger 25.

In addition the microprocessor 21 can receive through the contacts 19 setup instructions which are memorized in a program memory 26 in the satellite unit. For this purpose the base unit also has a microprocessor circuit 27 which receives operating commands through the control panel 15 and sends the appropriate instructions to the satellite unit through one or more of the contacts 19.

In accordance with the present invention the base unit also comprises a wireless transmission circuit 28 which connects with receiving circuits 29 located in each satellite unit. If required to allow the base unit to selectively address commands to the satellite units each satellite unit has a receiver 29 with programmable identification code for example by means of microswitches 31 to respond only to a transmission addressed to it.

Any transmission system can be selected. For example a radio transmission system can be employed or infrared if the receivers and transmitter are within optical range. In use the satellite units are initially inserted in their respected seats in the base unit. In this manner the internal accumulators are kept charged. When it is desired to administer a treatment the operator commands on the panel 15 the settings desired for a particular treatment. For example in general the EMS or TENS applications are characterized by the wave form generated on the electrodes, its minimum and maximum amplitude and its frequency. It might be desired to insert in the microprocessor circuit 27 the description of a series of treatment programs each defining a certain correlation of operating parameters and permit controlling through the controls 15 which program to transfer or set in the satellite unit or units 13 inserted in the base. The microprocessor unit in the satellite unit is thus set to perform a particular program by memorizing in the memory 26 what is received through the electrical contacts connecting it with the base unit.

Once a satellite unit is withdrawn from its seat in the base unit it becomes an independent unit producing the requested treatment on command.

When the program is set through the keyboard 15 the operator withdraws the satellite unit and applies it in position on the user's body. Once all the units necessary for treatment have been applied the operator commands starting of the treatment by means of the keyboard 15. In response thereto the base unit emits a start signal by means of the transmitter 28 and the satellite units receive it through the receiver 29. In this manner all the satellite units controlled begin simultaneously to perform the programmed duty.

In the same manner an end-of-treatment signal emitted by the base unit in response to a manual command on the keyboard 15 or a preset condition, for example the end of a treatment period, commands simultaneously extinction of all the satellite units.

In the case of treatments requiring the use only of a subassembly of the satellite units available in the equipment it may be thought that from the control panel 15 the satellite units could be divided in groups so that each group would be independently employed on a different user thus optimizing the full utilization of the equipment. In this case the start and stop signals would be sent to the correct satellite unit group thanks to the coding assigned to the satellite units.

Of course during treatment it would be easy even for the subject himself undergoing the treatment to identify and operate the controls 18 associated with each stimuli emission member.

Advantageously the base unit could comprise ultraviolet sterilization lamps 32 arranged in the compartment enclosed by the cover 16 to sterilize the part of the satellite units which come into contact with the user's body.

Naturally the above description of an embodiment applying the innovative principles of the present invention is given by way of non-limiting example of said principles within the scope of the exclusive right claimed here. For example the shape of the base unit and especially of the satellite units could change depending on the specific requirements and the type of stimuli produced. In particular each satellite unit could be provided as an individual member.

What is claimed is:

1. Electronic equipment for the production of stimuli for treatment of the human body comprising a base unit and at least one satellite unit with the satellite unit comprising a stimulous emission member, a rechargeable power supply battery, and means powered by the battery for producing an electric signal and applying the signal to said stimulus emission member, with the base unit comprising means of generating an actuation command and a de-actuation command signal for controlling production of the said electrical signal of the satellite unit, the base and satellite units being connected by wireless transmission means for transferring said command signals from said base unit to said satellite unit, the base unit further comprises at least one seat for reception of the satellite unit with the seat comprising a plurality of electrical contacts, and the satellite unit having thereon a like plurality of contacts for connection with the corresponding electrical contacts in the base unit to exchange electrical signals between the base unit and the satellite unit.

2. Equipment in accordance with claim 1 wherein some of the exchanged signals comprise power supplied by the base unit for recharging of the battery in the satellite unit.

3. Equipment in accordance with claim 1, including means in the satellite unit responsive to certain of the exchange signals for programming the operation of the satellite unit.

4. Equipment in accordance with claim 3, including a control panel on the base unit, and said certain of the exchange signals are emitted by the base unit in response to selections set on the control panel of the base unit.

5. Equipment in accordance with claim 1 wherein the satellite unit includes means for controlling regulation of the stimulus emitted by said emission member.

6. Equipment in accordance with claim 1 wherein said satellite unit is one of numerous like such units, said seat in said base is one of numerous such seats in said base for accommodating said satellite units, and said control signals emitted by the base unit are coded to be performed by but one of the satellite units selected from among the plurality thereof.

7. Equipment in accordance with claim 1 wherein the satellite unit comprises a microprocessor with program memory in which settings are memorized before sending of the activation control signal.

8. Equipment in accordance with claim 1 wherein the wireless transmission means comprises a radio.

9. Equipment in accordance with claim 1 characterized in that the base unit comprises ultraviolet lamps for radiant sterilization of the satellite unit when the latter is arranged in said seat.

10. Equipment in accordance with claim 1, wherein said satellite unit is one of numerous like such units, and said seat in said base is one of numerous such seats in said base for accommodating said satellite units.

11. Electronic equipment for production of stimuli for treatment of the human body, comprising a base unit and at least one satellite unit, with the satellite unit comprising a stimulus emission member, a rechargeable power supply battery, and means powered by the battery for producing an electric signal and applying the signal to said stimulous emission member, with the base unit comprising means of generating, respectively, actuation and de-actuation command signals for controlling production of said electrical signal of the satellite unit, the base and satellite units being connected by wireless transmission means for transferring said command signals from said base unit to said satellite unit, and the stimulus emission member comprising a pair of conducting electrodes engageable each with a different part of a human body, and operable for effecting electrical muscle or nerve stimulation.

12. Equipment in accordance with claim 1, wherein the satellite unit comprises two sub-units connected to each other by an electric wire, and each sub-unit having thereon one of said pair of conducting electrodes.

* * * * *